United States Patent [19]
Bergman et al.

[11] Patent Number: 5,053,340
[45] Date of Patent: Oct. 1, 1991

[54] IN VITRO TEST FOR DERMAL TOXIC PROPERTIES

[75] Inventors: Hyman C. Bergman, Los Angeles; Virginia C. Gordon; Christopher P. Kelly, both of Palm Springs, all of Calif.

[73] Assignee: National Testing Corporation, Palm Springs, Calif.

[21] Appl. No.: 315,317

[22] Filed: Feb. 24, 1989

[51] Int. Cl.$^5$ .................... G01N 13/00; G01N 21/29
[52] U.S. Cl. ........................................ 436/5; 73/64.3; 210/321.6; 422/56; 422/58; 422/101; 436/164; 436/530
[58] Field of Search ............... 73/64.3; 422/101, 56, 422/57, 58; 436/5, 530, 164; 210/321.6

[56] References Cited

U.S. PATENT DOCUMENTS

| | | | |
|---|---|---|---|
| 4,594,884 | 6/1986 | Bondi et al. | 73/64.3 |
| 4,771,004 | 9/1988 | Higuchi | 73/64.3 X |
| 4,835,102 | 5/1989 | Bell et al. | |
| 4,863,696 | 9/1989 | Seydek et al. | |

OTHER PUBLICATIONS

Draize et al., (1944) J. Pharmacol. Exp. Therap. 82: 377-390.
Wood et al., (1971) Br. J. Derm. 84: 320-325.
Kligman et al., (1967) Journal of Investigative Dermatology 49: (1): 78-94.
Blake-Haskins et al., (1986) J. Soc. Cosmet. Chem. 37: 199-210.
Fielder et al., (1987) Human Toxicol. 6: 269-278.
Finkelstein et al., (1962) J. Invest. Derm. 40: (63): 11-14.
Bettley et al., (1960) Br. J. Dermatology 72: 67-76.
Walz (1985) Fd. Chem. Toxic. 23(2): 199-203.
Bettley, (1960) British Medical Journal, pp. 1667-1679.
Harrold, (1959) J. Invest. Derm. 32: 581-588.
Van Scott et al., (1953) J. Invest. Derm. 21: 199-203.
Elias, (1988) Drug Development Research 13: 97-105.
Prottley et al., (1975) J. Soc. Cosmet. Chem. 26: 29-46.
Young et al., (1988) Toxic in vitro 2(1): 19-26.
Jacobs et al., (1987) J. Toxicol. 6(3): 215-225.
Crowe et al., (1987) J. Soc. Cosmet. Chem. 38: 451-455.
Oliver et al., (1986) Fd. Chem. Toxic 24(6-7): 513-515.
Finkelstein et al., (1965) Toxicology and Applied Pharmacology 7: 74-78.
Reinhardt et al., (1985) Fd. Chem. Toxic. 23(2): 247-252.
Rostenberg et al., (1939) J. Invest. Derm. 2: 93-97.
Prottey et al., (1972) J. Soc. Cosmet. Chem. 24: 473-492.
Kaminsky et al., (1986) J. Toxicol. 5(2): 81-87.
Frosch et al., (1979) J. Am. Acad. Derm. 1(1): 35-41.
Bettley, (1963) Br. J. Dermat. 75: 113-116.
Carter et al., (1965) Tox. Appl. Pharm. 7: 60-73.
Carabello, (1985) J. Toxicol. 4(2): 61-71.
Williams, (1984) Fd. Chem. Toxic. 22(2): 157-161.
Shopsis et al., (1985) Fd. Chem. Toxic. 23(2): 259-266.
Smyth et al., (1962) Indust. Hygiene Journal, pp. 95-107.
Miller et al. (1986) Fd. Chem. Toxic. 24:(6-7): 545-549.
Cockburn, (1986) Fd. Chem. Toxic. 24:(6-7): 597-598.
Stark et al., (1986) Fd. Chem. Toxic. 24:(6-7): 449-455.
Knox et al., (1986) Fd. Chem. Toxic. 24:(6-7): 457-463.
De Angelis et al., (1986) Fd. Chem. Toxic. 24:(6-7): 477-479.

(List continued on next page.)

*Primary Examiner*—Jill Johnston
*Attorney, Agent, or Firm*—Irell & Manella

[57] ABSTRACT

A membrane support, reagent and method determines, in vitro, skin irritation properties of individual compounds and/or mixtures is disclosed. The material to be tested is applied directly to the membrane support. The material may penetrate the membrane and diffuse into the reagent and cause a response, for example, the production of a precipitate. The test material may also alter or destroy the membrane and/or disrupt covalently linked dye molecules attached to the membrane and diffuse into the reagent to produce an additional or alternate response—for example, color. The sum of these two responses is proportional to the deleterious response elicited by the material on the human skin.

34 Claims, 2 Drawing Sheets

OTHER PUBLICATIONS

Parish, (1986) Fd. Chem. Toxic. 24:(6-7): 481-494.
Luepke et al., (1986) Fd. Chem. Toxic. 24:(6-7): 495-496.
Oliver et al., (1986) Fd. Chem. Toxic. 24:(6-7): 507-512, and 513-515.
Duffy et al., (1986) Fd. Chem. Toxic. 24:(6-7): 517-518.
Bosshard, (1985) Fd. Chem. Toxic. 23(2): 149-154.
Weinstein et al., (1988) J. Soc. Cosmet. Chem. 39: 315-320.
Riviere et al., (1986) Fundamental and Applied Toxicology 7: 444-453.
Pemberton et al., (1986) Br. J. Derm. 115: 45-46.
Ciuchta et al., (1978) Drug and Chemical Toxicology 1(3): 305-324.
Freeman et al., (1988) J. Am. Academy Dermatology 19(3): 496-502.
Scheuplein et al., (1970) J. Soc. Cosmet. Chem. 21: 853-873.
Prottey et al., (1976) Fd. Cosmet. Toxicol. 14: 425-430.
Ferguson et al., (1976) Fd. Cosmet. Toxicol. 14: 431-434.
Wenzel et al., (1983) Toxicology 29: 173-182.
Borenfreund et al., (1983) Annals New York Academy of Sciences 407: 416-419.
Faucher et al., (1978) J. Soc. Cosmet. Chem. 29: 323-337 and 339-352.
Imokawa, (1980) J. Soc. Cosmet. Chem. 31: 45-66.
Choman, (1963) J. Invest. Derm. 40: 177-182.
Oliver et al., (1988) Toxic. in Vitro 2(1): 7-17.
Imokawa et al., (1979) Contact Dermatitis 5: 357-366.
Tavss et al., (1988) J. Soc. Cosmet. Chem. 39: 267-272.
Blake-Haskins et al., (1986) J. Soc. Cosmet. Chem. 37: 199-210.
Idson et al., (1969) Toxicology and Applied Pharmacology 1969, Supplement No. 3, pp. 84-89.

IN VITRO TEST FOR DERMAL TOXIC PROPERTIES

TECHNICAL FIELD

This invention relates to the field of testing materials for their capacity to irritate human skin. More specifically, the invention relates to a device and a method for an in vitro test which can predict the ability of a specified material to cause temporary or permanent damage if placed in contact with the human skin.

BACKGROUND ART

In the United States and elsewhere in the technologically developed world it is customary and often legally mandated to assess the capacity of consumer products such as cosmetics, detergents, or other materials likely to be handled by the general public, to cause temporary or permanent damage to the human skin. It is clearly desirable and necessary to provide adequate labeling for corrosive skin irritants and even to restrict commercialization of products which contain components extremely damaging to the skin. It is estimated that more than 2 million tests are performed annually in the United States to examine the various cosmetic and household products for their potential harmfulness to the human skin. As in any instance where large numbers of tests need to be performed to screen for a particular property, it is desirable to have a testing procedure that is rapid, inexpensive, and reliable. An in vitro test would be most appropriate.

Such an in vitro test is not currently available for substances that might irritate the skin. The most commonly used screening procedure is the Draize rabbit skin test (Draize, J.H., et al., *J Pharmacol Exp Therap* (1944) 82:377). The disadvantages of this test are legion. (See for example, Weil, C.S., and Scala, R.A., *Toxicol Appl Pharmacol* (1971) 19:276-360; Phillips, L., et al., *Toxicol Appl Pharmacol* (1972) 21:369-382.) First, as an in vivo procedure, it involves some degree of maltreatment of test animals and considerable expense. Second, it is lengthy. The procedure consists of placing the substance to be tested onto a small square of gauze and applying this to the clipped trunk of the rabbit. After 24 hours the degree of irritation is scored subjectively.

Many attempts have been made to refine and improve this method using different exposure conditions, exposure times, and different animal models. (See for example, Roudabush, R.L., et al., *Toxicol Appl Pharmacol* (1965) 7:559; Wooding, W.M., and Opdyke, D.L., *J Soc Cosmet Chem* (1967) 18:809; Kligmann, A.M., and Wooding, W.M., *J Invest Dermatol* (1967) 49:78-94; Marzulli, F.N., *Toxicol Appl Pharmacol* (1965) 7:Suppl.2:79-85.) However, the inherent deficiencies of this in vivo testing approach make impossible the attainment of an inexpensive, rapid, reproducible, and predictive test for predicting skin irritation properties.

Although as in all animal tests, the correlation with effects of the materials in human subjects is imperfect, the Draize skin test has become the standard and any new in vitro tests should produce results similar to those of Draize. Thus correlation with Draize skin results can be used to evaluate the effectiveness of such a new test.

The clear desirability of an in vitro procedure has led a number of researchers to devise tests involving cell and organ cultures as opposed to whole animals. For example, the method of Benoit, J., et al., *Toxic in Vitro* (1987) 1:91, employs cultured human fibroblasts and uses the ability of a material to produce a cytotoxic effect as a measure of its skin irritation potential. Cytotoxic effects in cell culture as a measure of skin irritation has also been studied by Borenfreund, E., and Borrero, 0., *Cell Biol Toxicol* (1984) 1:55-65; Choman, B.R., *J Invest Dermat* (1984)40:177-182; and Scaife, M.C., *Fd Chem Toxic* (1985) 23:253-258. Helman, R.G., et al., *Fund and Appl Toxicol* (1984) 7:94-100, measured the leakage of cellular enzymes in cultured discs of mouse skin to evaluate the potential skin irritation of various chemicals. An additional method employs an isolated perfused skin flap for skin irritation measurements and was developed by Edmond, J., et al., *Fund and Appl Toxicol* (1986) 7:444-453.

These foregoing methods require either living cells in tissue culture or living organs in tissue culture. These methods suffer from lack of reproducibility, lack of objectivity, and lack of significant correlation with the Draize method.

Several other in vitro methods which do not use living cells have been developed to study skin irritation by surfactants. Some of these methods evaluate biophysical properties of the stratum corneum such as its swelling, and its permeability. Other methodologies determine the denaturation of proteins as indicators of potential skin irritation by surfactants. Blake-Haskins, J.C., et al., *J Soc Cosmet Chem* (1986) 37:199-210 related the irritancy of a surfactant to its ability to cause collagen matrices to swell and hold water. Ernst, R., *J Am Chem Soc* (1980) 57:93, measured the change in the activity of enzymes (i.e., denaturation) and related the decreased activity to the potential skin irritation of surfactants. While this method produced correlative results for some surfactants, many irritating solvents and preservatives did not alter the enzyme activity. The skin roughness caused by anionic surfactants was found to be related to their ability to denature protein materials (Imokawa, G., et al., *J Am Oil Chem Soc* (1975) 52:175). This method produced correlative results for anionic surfactants but not for cationic and nonionic surfactants and therefore, has not been shown to be universal in predicting skin irritation properties of surfactants. Finally, Kligman et al., *J Soc Cosmet Chem* (1988) 39:267, have shown that the pH of a solution of bovine serum albumin treated with a surfactant correlated with skin irritation. However, this relationship held for anionic surfactants but not for nonionic or cationic surfactants.

These methods fail to correctly mimic the simple three compartment model, which is the art-recognized model of skin irritation. Compartment one, the outer barrier or stratum corneum, which is a network of fibrous keratin and collagen molecules has a role to protect the epidermis and dermis from chemical assault and to provide the correct hydration for the skin. A change in this layer, such as the swelling of the stratum corneum, represents only the perturbation of this one compartment. Compartment two, the epidermis with its cells and intracellular components, the outer barrier. The third compartment, the dermis, lies beneath the epidermis and provides the vascularization and metabolic activity to nourish compartments one and two and is seldom involved in irritation except for extremely corrosive substances which destroy the stratum corneum and the epidermis. Skin irritation, registered as erythema and edema, requires changes in the structure and organization of macromolecules typical of compartments one and/or two when challenged with chemical irritants.

While the in vitro procedures above provide an alternative to the strictly in vivo approach of the Draize test, they do not achieve the simplicity and standardization that one expects from a new in vitro test. The method of the present invention offers such a test. It provides a quick, standard, reproducible, and objective measure of the capacity for any material to cause irritation in the human skin. It does not involve the use of animals and does not require the expense of maintaining, caging, and feeding them.

DISCLOSURE OF THE INVENTION

This invention provides a membrane support, a reagent, and a method for assessing the capacity of materials to cause temporary or permanent irritation to human skin. The magnitude of the total response produced by the membrane/reagent test system in the invention correlates to the severity of the skin irritation that will be caused by the test material on human skin. The membrane support and the reagent are defined or semidefined combinations of materials which have the advantages and properties of standard chemical reagents. The procedure is straightforward and rapid. A test material is applied directly to a membrane support. After incubation, the result can be assessed visually without instrumentation, or, if desired, can be quantitated using a variety of laboratory instruments that are commonly available in analytical laboratories.

Accordingly, in one aspect, the invention is directed to a method to determine the dermal toxicity of a test substance which comprises applying the substance to a membrane/reagent system. The membrane/reagent system comprises a membrane support to which crosslinked collagen and/or keratin may be bound. An indicator dye may additionally be covalently bound to the membrane support. In the membrane/reagent system of the invention, a reagent which may contain a precipitant and stabilizer contacts the membrane support to which the test substance is applied. The sample to be tested is applied to the membrane support on the side opposite the reagent. Test samples which are dermal irritants effect the release of dye from the membrane support and/or precipitation in the reagent. In the case of dye release, a skin or membrane irritant attacks the collagen and/or keratin network bound to the membrane. When dye is bound directly to a membrane support that is not bound to collagen and/or keratin, dye is released when its bond to the membrane support is broken. Formation of a precipitate, if any, is caused when the test substance penetrates the membrane support and causes pertubation of the higher order protein comprising the precipitant. The combined absorbance resulting from the release of the dye and/or precipitation in the reagent are then measured.

In another aspect, the invention is directed to a method to determine the phototoxicity of a test substance which method comprises irradiating a sample of the test substance with light and then applying the sample to a membrane/reagent system. Alternatively, a sample can be applied to a membrane/reagent system and the entire system irradiated.

In another aspect, the invention is directed to the membrane/reagent system employed in the method of the invention, which system may include a covalently bound indicator dye.

MODES OF CARRYING OUT THE INVENTION

A. Definitions

Figure 1:
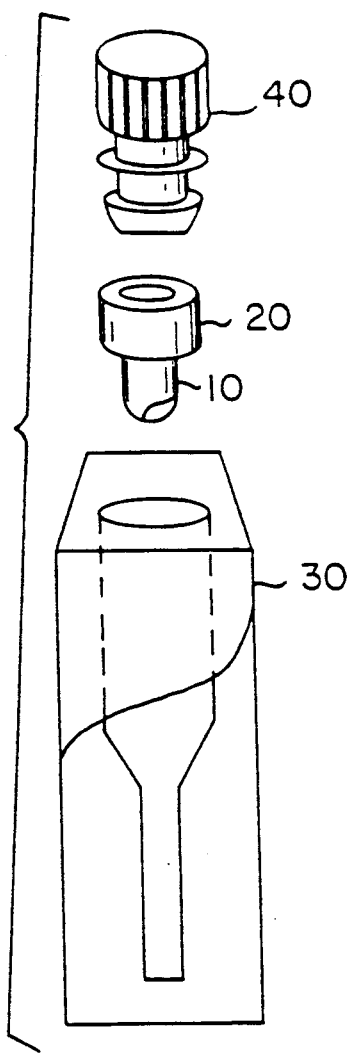
FIG. 1 is an exploded, partially cutaway view of the membrane/reagent system of the invention.

As used herein, toxicity of a material to the human skin or "dermal toxicity" refers to the ability of the material to cause negative responses in the human skin which take the form of either temporary or permanent damage to tissues. This toxicity is evidenced by causing pain, swelling or edema of the skin, and redness or erythema of the skin. Severe irritation, called corrosion, is evidenced by cracked or fissured skin and blister formation. Thus, the word toxicity or "toxic" in this context is defined broadly to include any discomfort or injury which results from a material coming in contact with the human skin.

As used herein, "phototoxicity" of a material to the human skin or "photodermatotoxicity" refers to the ability of a material to produce a toxic response in the skin, as described for "dermal toxicity" which would occur following skin exposure to light of sufficient intensity along with exposure to the light activated chemical in adequate amount. Two requisites of this response are light of 320 nm which does not produce a toxic response in the skin and a phototoxic reagent.

As used herein, "anti-irritant" is a material which can be used to protect an organ or tissue from "dermal toxicity" or "photodermal toxicity" due to a skin irritant or photoskin irritant. The "anti-irritant" may produce its effect by either complexing or reacting with the irritant and changing its "toxicity" and/or by blocking the reactive sites on the molecule, cell or organ physically and/or chemically.

"Clear aqueous liquid" refers to a liquid, usually a mixture, which is substantially water and is functionally transparent to light in the visible range. "Functionally transparent to light in the visible range" means that sufficient light is transmitted through the sample to permit full measurable readings "Membrane support", as used herein, refers to a prepared membrane to which a test sample is applied. The membrane support can be prepared from a base support membrane with or without bound keratin, collagen, and/or mixtures of these proteins, and may or may not also have indicator dye bound to it. A partially processed natural membrane or animal skin can also be used as a membrane support.

"Reagent" refers to the reaction mixture which contacts a membrane to which a sample is applied.

"Compatible" conditions of pH and/or ionic strength refers to ranges of these parameters which are consistent with the property of the membrane support to only release dye molecules when in the presence of a skin irritant and the property of the reagent to precipitate only in the presence of a skin irritant.

"Dermal irritant" refers to a substance which is capable of producing toxicity to the human skin when placed in contact with it and is measured by the degree of erythema and edema observed in the human skin.

B. General Description

B.1. General Parameters of the Testing Procedure

The present invention provides a membrane/reagent system which, when exposed to a substance to be tested for dermal toxicity, produces a response which is measurable qualitatively or quantitatively in proportion to the dermal toxicity of the sample to be tested. The direct response of applying the sample to the membrane/reagent system is the formation of color and/or precipitate in the reagent due to either actual attack of the membrane support by the test substance thereby causing release of any associated dye molecules into reagent and/or penetration of the membrane support thereby causing precipitation in the reagent. The magnitude of the response can be assessed using a variety of techniques that are described in detail below. The formation of the color in a very rough sense mimics the response produced in the skin as erythema. The formation of the precipitate mimics in a very rough sense the response produced in the skin as edema. Therefore, the total response of the membrane/reagent system to the substance to be tested can be used as a predictor of the response of skin tissue or other membranes.

B.2. The Membrane

Figure 2:
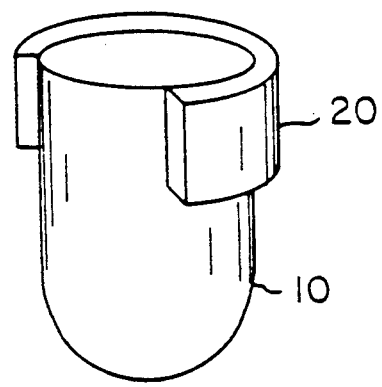
FIG. 2 is a partially cutaway perspective view of the membrane support well.

As seen in FIGS. 1 and 2, membrane support 10 is formed from a colored or uncolored pliable membrane. The membrane is chosen so as to mimic the particular skin or membrane that would be irritated by an irritant. The membrane support is formed into an individual small well held by a ring 20 so that the test substance applied inside the membrane well can be inserted down into a cuvette 30 containing reagent. Stopper 40 can be inserted into the top of the cuvette to seal the membrane support well containing the test substance.

The membrane itself is a combination of a semipermeable support membrane, such as cellulose or nitrocellulose, to which keratin and/or collagen can be optionally bound, using, for example, a bifunctional crosslinking reagent such as dimethylsuberimidate. A carboxylic dye can then optionally be covalently attached via an ester or other convenient linkage to the keratin and/or collagen or to a bare base support membrane. The resulting membrane support mimics the stratum corneum barrier of the skin.

According to the present invention, the membrane support can also be constructed without bound keratin/collagen so as to mimic mucous membrane such as the buccal, vaginal, or penis membrane.

In addition to the above-described synthetic membranes, animal membranes and/or skin such as snake or pig skin can be used for the base support membrane to which the dye can be covalently attached if desired.

Dyes suitable for use in the present invention include carboxylic dyes which can be covalently linked to a membrane support. Examples are Safrannin 0, Carmine, Erythrosin B, and malachite green oxalate (Aldrich), all of which can be covalently attached via an ester or other convenient linkage to the membrane support, for example, by using a bifunctional reagent. Fluorescent dyes, for example, Rose Bengal, may also be covalently attached to the membrane support. Dye so linked to a membrane support is able to be released after contact with corrosive dermal irritants as the higher order matrices and integrity of the keratin and/or collagen matrix break down or degrade due to the irritant, thereby releasing discrete amounts of collagen and/or keratin and associated dye molecules. In cases where the membrane support comprises only a base support membrane such as cellulose, contact with a dermal irritant can disrupt the covalent linkages of the cellulose causing release of any associated dye molecules.

A lipid component can also be added to a keratin/collagen cross-linked synthetic membrane support by covalently attaching, coupling, and/or binding a fatty acid or cholesterol or acylceramide to the cross-linked membrane support. This additional component which is present in all human skin, changes the permeability characteristics of the synthetic membrane support. The amount and kind of lipid in human skin varies widely depending on body location, diet, ethnic variability, and other parameters. Therefore, any lipid should only be included in the basic simple synthetic membrane when the importance of this component in the skin is being evaluated.

When a dermal irritant which is to be evaluated by the method of the invention is applied to the membrane support well (FIGS. 3c, 3d), the irritant can diffuse through the membrane support and, if sufficiently irritating, can disrupt the membrane or any cross-linked dye keratin/collagen matrix causing release of portions of the membrane material along with any covalently linked soluble dye molecules into the reagent. The greater the disruption of the membrane, the greater the release of the carboxylic dye into the reagent, and the greater the potential exists for dermal irritation to be produced by the test substance.

B.3. The Reagent

The reagent is used in the form of a clear aqueous liquid that can be exposed to the test substance contained within the membrane support well in instances when the membrane support is penetrated by the test substance. In such instances, the active ingredients of the reagent will precipitate in the presence of a dermal irritant.

The reagent mixture itself is a composition of proteinaceous materials, amino acids, carbohydrates, and ionic compounds which mimics the response of the epidermal layer of human skin tissue when contact is made with the materials to be tested.

The clear aqueous liquid reagent of the invention contains solutes or colloidal particles which will remain in solution until a dermal irritant diffuses through the membrane into the solution and produces precipitation. To achieve this, the reagent contains at least one precipitant and at least one stabilizer and is maintained at a compatible pH and ionic strength.

Precipitation and/or color released from the membrane represents the desired response of the membrane/reagent system to a dermal irritant.

Materials useful as effective precipitants include the globular proteins and are best employed as mixtures of several different globulins such as G1, G2, and G3. The total globulin content in the complete reagent is preferably in the range of about 0.001% to 10% depending on the source and class of the globulins. Alternate precipitants include, for example, macroglobulins, glycosaminoglycans, and mucoproteins.

Stabilizers prevent premature aggregation of the precipitant and may make the extent and the form of the precipitant more reproducible. Suitable stabilizers include, for example, amino acids such as glycine, glutamine, proline, peptides, and non-globulin proteins such as albumin. A wide range of concentrations and combinations of stabilizers can be used with the present invention. In general, total stabilizer concentration is preferably in the range of about 0.001% to 10%.

Compatible pH range and ionic strength may be maintained by adjusting the buffering capacity and ionic strength of the precipitants and stabilizers used. Also, suitable pH and ionic strength can also be achieved by using ionic compounds or buffers. A compatible pH range is between about 2 and 9. Suitable buffers in this range include phosphate salts, acetate salts, Tris-Cl, borate, and a variety of other compounds known in the art. Ionic strength can vary over a wide range of about 0.05 M to 0.5 M.

It is desirable, though not absolutely necessary, to include enhancers in the reagent which interact with the molecules of the precipitant to increase its aggregation in the presence of dermal irritants. Such enhancers are typically glycoproteins, mucopolysaccharides, carbohydrates, and lipids. The desired range of these enhancers is typically about 0 to about 10%.

In the foregoing paragraphs, applicants have set forth the parameters required to define the membrane support and reagent materials using predetermined amounts of available substances. Two natural materials that can be used to prepare the reagent are egg whites and jack beans. The preparations of reagent from these materials can be made by using salt solutions as a diluent. The extracting solutions, if such natural materials are used, may not need to contain precipitants of stabilizers, as these are found in the natural materials themselves.

It is also possible to achieve the results of a workable system by using membranes from natural sources. Skin membrane can be produced by dying the skin shed from a snake, and such a skin membrane behaves in a way very similar to the dyed prepared membrane described above. In this case, it is not necessary to cross-link the keratin protein naturally present because it is already extensively cross-linked naturally.

It is further possible and sometimes desirable to formulate the reagent without any precipitant and stabilizer in order to evaluate the effect of a dermal irritant on the stratum corneum. In such an application the release of dye into the reagent serves as a measure of dermal toxicity.

B.4. The Method

A major virtue of the method of this invention is its simplicity. The crux of the procedure is the application of the material to be tested to a synthetic or natural membrane support and exposure of the membrane support to a reagent which is sensitive to chemical irritants. The results can be read quantitatively by direct measurement of the amount of dye released and/or precipitate formed.

The amount of the colored dye released and/or the amount of the precipitate formed can be measured using standard absorbance readings obtained with a colorimeter or spectrophotometer with a visible light source between 350 and 710 nm. The reagent and sample "blanks" can be used to correct for absorbance caused by the presence of the reagent itself or by the sample itself. The absorbance of both the sample and reagent blank are subtracted from that of the test sample.

Light scattering due to turbidity can be quantitated as absorbance from 340 to 710 nm. The wavelengths of 350 to 710 nm were chosen to coincide with the wavelength intensity distribution of the dye attached to keratinized membrane. The dye released is best quantitated in this wavelength region.

In instances where the membrane support is dyed and the reagent contains a precipitant, the release of the dye from the membrane can be quantitated separately from the amount of precipitate formed. The absorbance at 340 nm measures only the turbidity or precipitation of the reagent but no color change, while absorbance taken at 580 nm measures approximately 60% of the total turbidity of measuring absorbance at both 340 nm and 610 nm, and subtracting the 340 nm absorbance (turbidity) from the 610 nm absorbance (turbidity and dye), the quantitation of dye released from the membrane can be accomplished. Alternatively, if the reagent is formulated without a precipitant and stabilizer, dye release can be measured directly.

The amount of precipitate can be quantitated separately from the amount of dye released by measuring the mass of the precipitate directly by centrifugation or by nephelometry where the color makes no contribution to the reading of turbidity. Alternatively, the ingredient which forms the precipitate could be labeled with a radioisotope or a fluorophore and after separation of the precipitate, the amount of the precipitate quantitated by means appropriate to the nature of the label. Additionally, if a membrane support without dye is used, precipitate can be directly measured.

The amount of dye released can also be assessed quantitatively using a dye labeled either with a radioactive isotope or with a fluorescence tag. A fluorescent dye could also be used for this purpose. The supernatant and the precipitate can be separated and the amount of label read in the desired fraction by means appropriate to the nature of the label.

The method of the invention can also be used to determine the dermal irritation of phototoxic materials. Two approaches have been used to determine phototoxic effects. In the first approach, test materials are first exposed to UV light at specific intensities and specific intervals outside the membrane/reagent system of the invention. The light-exposed material is then evaluated by using the membrane/reagent system of the invention for production of color and/or precipitate. The irritation produced by the phototoxic material without exposure to light is also measured. The increased irritation or phototoxicity of the material exposed to UV light is due to the photo-breakdown products of the test sample.

In the second approach to measuring dermal irritation of phototoxic materials, a sample of phototoxic material is applied to the membrane/reagent system, the entire system is then exposed to discrete quantities of UV light, and the change in the production of color and/or precipitate is quantitated. The irritation of the sample which is not exposed to light is also measured, and the color formation and/or precipitate production is quantitated. The incremental change in the irritation response due to irradiation as compared to the irritation response in the absence of irradiation is defined as the "phototoxic dermal irritation" of the test substance.

The method of the invention can also be used to identify and quantitate the anti-irritancy of materials. Anti-irritants protect a tissue, organ, or molecule from the irritating effects of a test substance. The membrane support of the membrane/reagent system can be pretreated with an unknown potential anti-irritant material. A known irritant can then be applied to the membrane support well and the production of color and/or precipitation quantitated. A reduction in the response produced by the irritant when compared to the response of the test substance when no anti-irritant was used to treat the membrane support is indicative of protection by the potential anti-irritant material and its anti-irritancy. The anti-irritancy of a material can also be determined by premixing a sample containing a potential anti-irritant and a known irritant and then applying the resulting mixture to the membrane/reagent system. A reduction in the response produced by the irritant/anti-irritant with respect to the response produced by the irritant alone is again indicative of the anti-irritancy potential of the anti-irritant. The optimal combination of the anti-irritant and the irritant can be determined by varying the ratios of combination of these materials.

The potential of a test material to produce irritation of the mucosal membrane can also be determined by the method of the invention. The membranes are structurally unlike the dermal stratum corneum, and so a base support membrane is used without keratin/collagen or dye bound to it. This membrane permits diffusion of the test sample into the reagent and the production of turbidity indicates the degree of irritation.

B.5. Evaluation of the Results

As set forth above, it is desirable to have a direct correlation between the results of the test as performed by the method of the invention and the capacity of a material to irritate the human skin. However, results of human experience for a large number of irritants for which testing is desired is not available. The results of Draize testing on large number of substances is readily available. Therefore, a threshold criterion for predictive validity of the testing procedures of the invention is correlation of its results with those of the Draize testing on the same substances.

Figure 4:
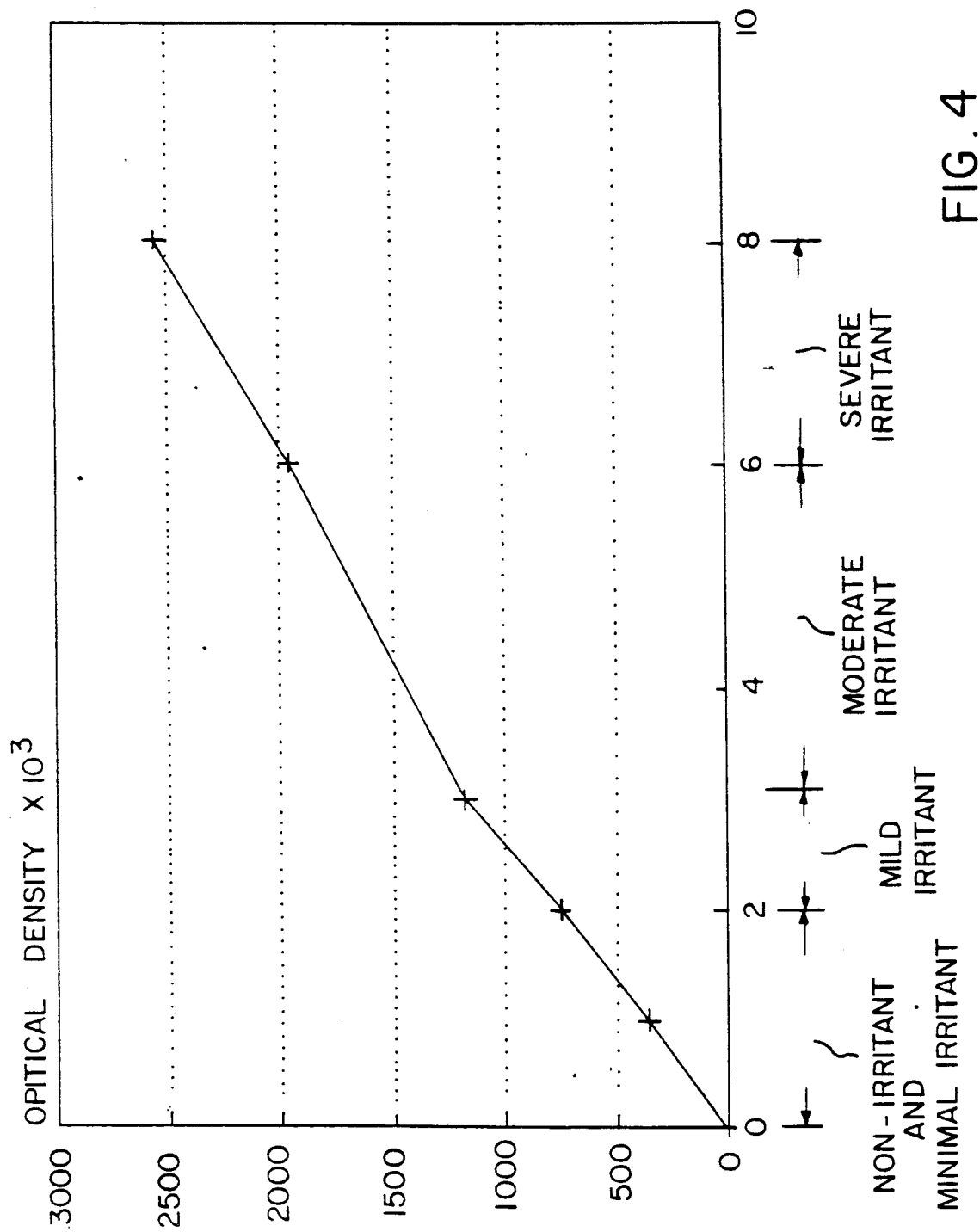
FIG. 4 shows the results of the method of the invention as correlated with the Draize rabbit skin test.

Accordingly, calibration curves, FIG. 4, have been prepared showing the relationship between the absorbance readings obtained using the membrane/reagent system of the present invention and 580 nm light to assess the color and turbidity caused by test substances with the results of the Draize test. Similar procedures may be used to calibrate other primary results using criteria such as absorbance at other wavelengths, nephelometric readings, radioactivity, and fluorescence.

Typically, the absorbance at 580 nm due to the response of a test material applied to the membrane/reagent system follows a dose response pattern with absorbance increasing with increased concentration of test substance. At a level characteristic of each individual test material, a plateau in absorbance measurement is observed. This is expected behavior in absorbance measurements, and, therefore, it is possible to establish a reference position on the absorbance curve being read for each material tested. Testing using the method of the invention is done using undiluted materials unless dilutions were studied in the Draize rabbit patch test.

Each test substance is tested at several levels by making absorbance readings for sample sizes of, for example, 30 ul, 50 ul, and 100 ul. The absorbances obtained at these sample sizes can be classified by comparing them with the absorbances of known irritants with well-established dermal irritation. These classifications can be used to correlate the results so obtained with the Draize rabbit patch test results.

C. Examples

The following examples are intended to illustrate but not to limit the invention.

C.1. Preparation of the Reagent Mixture

Globulins extracted from cucurbita pepo, recrystallized from deionized water, and lyophilized were used as a starting source of the reagent. This powder was solubilized in a buffered salt solution containing 10% sodium chloride, 3% sodium borate, and 0.1% sodium ethylenediaminetetraacetic acid buffered with glacial acetic acid to pH 8.0. The resultant solution was filtered through a Whatman #1 filter paper and used as a stock solution. Immediately prior to use, the pH was adjusted to 7.0 and the solution was used as the reagent mixture.

An alternative preparation of reagent mixture from jackbean meal is shown in Table 1.

TABLE 1

| Compound | Concentration |
| --- | --- |
| $CaCl_2$ | 0.02% |
| KCl | 0.04% |
| $MgSO_4$ | 0.01% |
| $NaH_2PO_4H_2O$ | 0.01% |
| NaCl | 0.2M |
| isoleucine | 0.002% |
| glutamine | 0.03% |
| leucine | 0.002% |
| lysine: HCl | 0.004% |
| tyrosine | 0.002% |
| valine | 0.002% |
| NaOAc | 0.1M |
| EDTA | 0.1% |
| N-ethylmaleimide | 0.01% |
| $NaN_3$ | 0.02% |
| glucose | 0.1% |
| globulin $G_1$ | 0.1–0.2% |
| mucopolysaccharide | 0.1–0.15% |
| albumin | 0.1–0.3% |
| carbohydrates | 0.2–0.3% |
| lipids | 0.3–0.5% |
| saponins | 0.001–0.01% |

TABLE 2

| Compound | Concentration |
| --- | --- |
| NaOAc | 0.07M |
| NaCl | 0.15M |
| EDTA | 0.07% |
| N-ethylmaleimide | 0.07% |
| $NaN_3$ | 0.015% |
| $CaCl_2$ | 0.014% |
| KCl | 0.028% |
| $MgSO_4$ | 0.007% |
| $NaH_2PO_4H_2O$ | 0.007% |
| lysine: HCl | 0.007% |
| isoleucene | 0.001% |
| tyrosine | 0.001% |
| glutamine | 0.021% |
| valine | 0.001% |
| conalbumin | 3% |
| ovalbumin | 22% |
| lipids | 0.4% |
| carbohydrates | 0.3% |
| ovomucoid | 4% |
| globulin $G_1$ | 0.5–1% |
| globulin $G_2$ | 0.5–2% |
| globulin $G_3$ | 0.2–2% |
| glucose | 0.1% |

C.2. Preparation of the Membrane Support

Figure 3A:
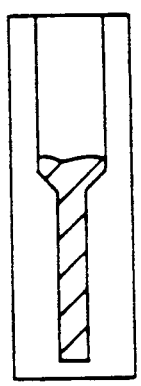
FIGS. 3a–3d are a series of four cross-sectional side views showing the device of FIG. 1 in action providing an in vitro indication of dermal toxicity.
Figure 3B:
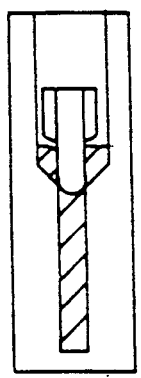
Figure 3C:
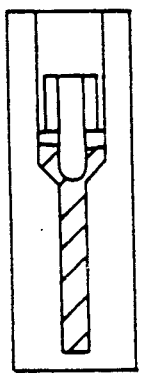
Figure 3D:
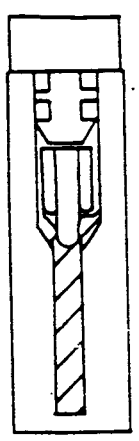

Membrane dialysis sheet for exclusion of molecules larger than 12,000 to 14,000 MW is first immersed in a solution of 20% keratin derived from pig skin with 0.1% glutaraldehyde. The membrane sheet is then incubated for 2 hours at 25° C. and rinsed with deionized water. The resulting keratinized membrane support is then immersed in a solution of 5% Saffranin 0 with 0.1% glutaraldehyde or a bifunctional cross-linking reagent such as dimethylsuberimidate. The membrane support is dyed for 20 minutes and is rinsed overnight in distilled water. The dyed-keratinized membrane support is then dried and stored in moisture-tight containers at 4° C. Squares 2 cm by 2 cm are cut and inserted through a 1 cm-tall plastic ring as shown in FIGS. 1 and 2. The test samples are inserted through the top opening of the membrane support well as shown in FIG. 3(c).

Membrane supports used to mimic response of mucous membrane can be prepared directly from the membrane dialysis sheets as described above without treating with keratin or dye.

C.3. Results

C.3.a. Results of Calibrated Study

In one protocol, 100 ul of test sample was used in one membrane suspended in a total volume of 1 ml of reagent. The optical density at 580 nm was read in a Beckman DU-8B spectrophotometer at 2 hours and used as a criterion for dermal toxicity. The results, shown in FIG. 4, show a linear correlation with Draize test results.

Based on the absorption produced by dilutions of sodium lauryl sulfate, a well-established and thoroughly studied dermal irritant (Wood, D.C.F., and Bettley, F.R., *Brit J Dermatol* (1971) 84:320), test substances were placed in categories of:

| | |
|---|---|
| non-irritant and minimal irritant | <0.8 O.D. |
| mild irritant | 0.8–1.2 O.D. |
| moderate irritant | 1.2–1.89 O.D. |
| severe irritant | >1.9 O.D. |

Sodium lauryl sulfate at 3% produced a moderate/severe dermal irritation in vivo and an absorption reading of 1.9 O.D. by the method of the invention. Sodium lauryl sulfate at 0.5% produced a mild/moderate dermal irritation in vivo and an absorption reading of 1.2 O.D. by the method of the invention. Sodium lauryl sulfate at 0.3% produced a minimal/mild irritation in vivo and an absorption reading of 0.8 O.D. by the method of the invention.

The results in Table 3 below show absorbance values for 100 ul (liquid) or 100 mg (solid) sample size and the classification of the results using the above indicated calibration. These classifications are compared with those reported by various researches using the in vivo Draize rabbit patch test. Dilutions prepared are indicated next to the sample name.

As can be readily seen, in 29 of these 32 samples the results obtained by the method of the invention were substantially identical to those obtained by the in vivo test. In two of the remaining three samples the results were only different by one classification. In only one case was there a difference of two classifications.

These data demonstrate the results obtained by the method of the invention correlate with human data as well as those obtained from the Draize skin test.

TABLE 3

| Sample | O.D. 580 nm | Classif. | In Vivo | Ref.* |
|---|---|---|---|---|
| Propylene glycol | 0.03 | minimal | minimal | 3 |
| Sucrose | 0.01 | minimal | minimal | 4 |
| Methyl paraben | 0.06 | minimal | mild | 2 |
| Propyl paraben | 0.04 | minimal | minimal | 4 |
| Thioglycolic acid | 0.10 | minimal | minimal | 1 |
| Tiethanolamine | 0.09 | minimal | minimal | 4 |
| Phenol | 1.99 | severe | severe | 3 |
| Benzalkonium Cl | >2.0 | severe | severe | 2 |
| Sodium lauryl SO$_4$ | >2.0 | severe | severe | 2 |
| Night cream | 0.01 | minimal | minimal | 5 |
| Oleic acid | 0.43 | minimal | minimal | 1 |
| Sodium laureth SO$_4$ | 0.98 | mild | mild | 6 |
| Hydrochloric acid | >2.0 | severe | severe | 6 |
| Shampoo | 1.43 | moderate | moderate | 5 |
| Conditioner | 0.05 | minimal | minimal | 5 |
| Butanol | 0.09 | minimal | minimal | 8 |

TABLE 3-continued

| Sample | O.D. 580 nm | Classif. | In Vivo | Ref.* |
|---|---|---|---|---|
| Alpha olefin SO$_4$ | 1.67 | moderate | moderate | 7 |
| Octanol | 0.06 | minimal | mild | 8 |
| NaCl | 0.11 | minimal | minimal | 2 |
| Xylene | 0.09 | minimal | moderate | 1 |
| Acetone | 0.11 | minimal | minimal | 8 |
| Benzoic acid | 1.07 | mild | mild | 4 |
| Phenoxyethanol | 1.41 | moderate | moderate | 4 |
| Oxalic acid | 1.76 | moderate | moderate | 1 |
| Mineral oil | 0.02 | minimal | minimal | 4 |
| NaOH (25%) | >2.0 | severe | severe | 6 |
| NH$_3$OH (2.5%) | 0.03 | minimal | minimal | 6 |
| Isopropanol | 0.02 | minimal | minimal | 4 |
| Formaldehyde | 1.01 | moderate | moderate | 4 |
| Tween 20 | 0.89 | mild | mild | 7 |
| Saline | 0.03 | minimal | minimal | 5 |
| Dimethylsulfoxide | 0.04 | minimal | minimal | 4 |

*References:
1. Independent Testing Laboratory
2. I. F. H. Purchase et al., (1988) ATLA, 14:184–242.
3. Guillot, J. P. et al., (1982) Fd. Chem. Tox., 20:563–572.
4. M.S.D.S. results from Sigma Chemical Company
5. Industrial Testing Laboratory
6. Kligman, G. H. et al., (1988) J. Soc. Cosmet. Chem., 39:267–272.
7. Industrial Testing laboratory
8. H. F. Smyth and G. P. Carpenter, (1962) Am Industrial Hyg., 23:95–107.

C.3.c. Results of Phototoxic Study

Coal tar was applied to dyed membrane/reagent system as described above and was exposed to ultraviolet light for 24 hours. The optical density produced at 580nm was measured. Coal tar was also applied to the dyed membrane/reagent system which was not exposed to ultraviolet light, and the optical density at 580 nm measured. This experiment was repeated for methoxysalen, chlorpromazine, and NaCl. The first three test materials produced an increased response with exposure to the light. The NaCl which is not a phototoxic material did not produce an increased response in the presence of light.

As seen in Table 4, this method distinguished the three phototoxic materials from the material which was not phototoxic.

TABLE 4

| | non-irradiated | | irradiated | |
|---|---|---|---|---|
| Sample/Concentration | O.D. | Classif. | O.D. | Classif. |
| coal tar 1% | .05 | minimal | 0.421 | mild |
| methoxysalen 0.01% | .09 | minimal | 0.679 | mild |
| chlorpromazine 0.01% | .11 | minimal | 0.511 | mild |
| NaCl | .11 | minimal | 0.11 | minimal |

C.3.d. Results of Anti-Irritant Study

Preparation A containing 5% benzoyl peroxide, 5% PEG 400, and 90% water was prepared with and without a dimeric acid ester, which is thought to be an anti-irritant. The dimeric acid ester anti-irritant mixed into preparation A reduced the irritation of preparation A in the Draize rabbit skin test. Both preparations were applied directly to the membrane/reagent system. The test was conducted as described above, and the optical density at 580 nm was read after 24 hours of incubation. As seen in Table 5, the irritation without the anti-irritant was mild; after addition of the anti-irritant to preparation A, the irritation was minimal.

TABLE 5

| Sample | O.D. | Classif. |
|---|---|---|
| Preparation A | 0.561 | mild |
| Preparation A with anti-irritant | 0.084 | minimal |

A second experiment was conducted to determine the amount of anti-irritant necessary to reduce the irritation from mild to minimal. Dimeric acid ester anti-irritant was mixed into preparation A in amounts 0.11% to 0.2%, 0.4%, 0.8% and 1.0% of the total amount. As shown in Table 6, 0.8% of anti-irritant produced a substantial reduction in the irritation of the preparation.

TABLE 6

| Sample | O.D. | Classif. |
|---|---|---|
| Preparation A (Control) | 0.563 | mild |
| A + 0.1% anti-irritant | 0.466 | mild |
| A + 0.2% anti-irritant | 0.433 | mild |
| A + 0.4% anti-irritant | 0.212 | minimal |
| A + 0.8% anti-irritant | 0.106 | minimal |
| A + 1.0% anti-irritant | 0.091 | minimal |

In summary, the invention provides a convenient, inexpensive screening procedure to obtaining preliminary data with respect to dermal irritation of a material. Results obtained were comparable to those obtained from the procedures involving whole animals.

We claim:

1. A method for determining the toxicity of a material to human skin or membrane which method comprises:
   (a) applying said material to one face of a membrane support which mimics human skin or membrane to be tested comprising a base membrane support to which is bound a composition selected from the group consisting of cross-linked keratin, cross-linked collagen and mixtures thereof to which a dye is covalently bound, wherein said dye is released from said covalent bonding in the presence of a dermal irritant, said membrane support being in contact at its opposite face with a reagent containing at least one precipitant being present in a concentration effective in precipitation in the presence of a dermal irritant, and said reagent further containing at least one stabilizer present in a concentration effective to prevent precipitation of the precipitant in the absence of a dermal irritant, said reagent comprising an aqueous medium of pH and ionic strength compatible with said membrane support;
   (b) measuring at least one of the amount of dye released into the reagent and the amount of precipitate formed in the reagent; and
   (c) comparing said at least one of the amounts of dye and precipitate with at least one of the amount of dye and precipitate released using comparable amounts of a known dermal irritant.

2. A method to determine the phototoxicity of a material to human skin or membrane, which method comprises:
   (a) exposing said material to ultraviolet light;
   (b) applying said material to one face of a membrane support which mimics human skin or membrane to be tested comprising a base membrane support to which is bound a composition selected from the group consisting of cross-linked keratin, cross-linked collagen and mixtures thereof to which a dye is covalently bound, wherein said dye is released from said covalent bonding in the presence of a dermal irritant, said membrane support being in contact at its opposite face with a reagent containing at least one precipitant being present in a concentration effective in precipitation in the presence of a dermal irritant and said reagent further containing at least one stabilizer present in a concentration effective to prevent precipitation of the precipitant in the absence of a dermal irritant said reagent comprising an aqueous medium of pH and ionic strength compatible with said membrane support;
   (b) measuring at least one of the amount of dye released into the reagent and the amount of precipitate formed in the reagent; and
   (c) comparing said at least one of the amounts of dye and precipitate with at least one of the amount of dye and precipitate released in the absence of exposing said material to ultraviolet light.

3. A method to determine the phototoxicity of a material to human skin or membrane which method comprises:
   (a) applying said material to one face of a membrane support which mimics human skin or membrane to be tested comprising a base membrane support to which is bound a composition selected from the group consisting of cross-linked keratin, cross-linked collagen and mixtures thereof to which a dye is covalently bound, wherein said dye is released from said covalent bonding in the presence of a dermal irritant, said membrane support being in contact at its opposite face with a reagent containing at least one precipitant being present in a concentration effective in precipitation in the presence of a dermal irritant and said reagent further containing at least one stabilizer present in a concentration effective to prevent precipitation of the precipitant in the absence of a dermal irritant said reagent comprising an aqueous medium of pH and ionic strength compatible with said membrane support;
   (b) exposing said treated membrane support to ultraviolet light;
   (c) measuring at least one of the amount of dye released into the reagent and the amount of precipitate formed in the reagent; and
   (d) comparing at least one of the amount of dye and precipitate with the amount of dye and/or precipitate released in the absence of exposing said material to ultraviolet light.

4. A method to determine the effect of a test material on the ability of an irritant to exhibit dermal toxicity which method comprises:
   (a) combining said test material with said irritant to obtain a mixture;
   (b) applying said material to one face of a membrane support which mimics human skin or membrane to be tested comprising a base membrane support to which is bound a composition selected from the group consisting of cross-linked keratin, cross-linked collagen and mixtures thereof to which a dye is covalently bound, wherein said dye is released from said covalent bonding in the presence of a dermal irritant, said membrane support being in contact at its opposite face with a reagent containing at least one precipitant being present in a concentration effective in precipitation in the presence of a dermal irritant and said reagent further containing at least one stabilizer present in a concentration effective to prevent precipitation of the precipitant in the absence of a dermal irritant said reagent comprising an aqueous medium of pH and ionic strength compatible with said membrane support;

(c) measuring at least one of the amount of dye released into the reagent and the amount of precipitate formed in the reagent; and (d) comparing at least one of the amount of dye and precipitate with the amount of dye and/or precipitate released using comparable amounts of a known dermal irritant in said mixture.

5. A method for determining the toxicity of a material to human skin or membrane which method comprises:

(a) applying said material to one face of a membrane support which mimics human skin or membrane to be tested comprising a base membrane support to which is bound a composition selected from the group consisting of cross-linked keratin, cross-linked collagen and mixtures thereof to which a dye is covalently bound wherein said dye is released from said covalent bonding in the presence of a dermal irritant, said membrane support being in contact at its opposite face with a reagent which comprises an aqueous medium of pH and ionic strength compatible with said membrane support;

(b) measuring the amount of dye released into the reagent; and (c) comparing the amount of dye released with the amount of dye released using comparable amounts of a known dermal irritant.

6. A method for determining the toxicity of a material to human skin or membrane which method comprises:

(a) applying said material to one face of a membrane support which mimics human skin or membrane to be tested comprising a base membrane support to which is bound a composition selected from the group consisting of cross-linked keratin, cross-linked collagen and mixtures thereof, said membrane support being in contact at its opposite face with a reagent containing at least one precipitant present in a concentration effective in precipitating in the presence of a dermal irritant and at least one stabilizer present in a concentration effective to prevent precipitation of the precipitant in the absence of a dermal irritant, said reagent comprising an aqueous medium of pH and ionic strength compatible with said membrane support;

(b) measuring the amount of precipitate formed in the reagent; and (c) comparing the amount of precipitate formed with the amount of precipitate released using comparable amounts of a known dermal irritant.

7. A method for determining the phototoxicity of a material to human skin or membrane which method comprises:

(a) exposing said material to ultraviolet light;

(b) applying said material to one face of a membrane support which mimics human skin or membrane to be tested comprising a base membrane support to which is bound a composition selected from the group consisting of cross-linked keratin crosslinked collagen and mixtures thereof, said membrane support being in contact at its opposite face with a reagent containing at least one precipitant present in a concentration effective in precipitating in the presence of a dermal irritant and at least one stabilizer present in a concentration effective to prevent precipitation of the precipitant in the absence of a dermal irritant, said reagent comprising an aqueous medium of pH and ionic strength compatible with said membrane support;

(c) measuring the amount of precipitate formed in the reagent; and (d) comparing the amount of precipitate formed with the amount of precipitate released in the absence of exposing said material to ultraviolet light.

8. A method for determining the phototoxicity of a material to human skin or membrane which method comprises:

(a) applying said material to one face of a membrane support which mimics human skin or membrane to be tested comprising a base membrane support to which is bound a composition selected from the group consisting of cross-linked keratin crosslinked collagen and mixtures thereof, said membrane support being in contact at its opposite face with a reagent containing at least one precipitant present in a concentration effective in precipitating in the presence of a dermal irritant and at least one stabilizer present in a concentration effective to prevent precipitation of the precipitant in the absence of a dermal irritant, said reagent comprising an aqueous medium of pH and ionic strength compatible with said membrane support;

(b) exposing said treated membrane support to ultraviolet light;

(c) measuring the amount of precipitate formed in the reagent; and (d) comparing the amount of precipitate formed with the amount of precipitate released in the absence of exposing said material to ultraviolet light.

9. A method to determine the effect of a test material on the ability of an irritant to exhibit dermal toxicity which method comprises:

(a) combining said test material with said irritant to obtain a mixture;

(b) applying said material to one face of a membrane support which mimics human skin or membrane to be tested comprising a base membrane support to which is bound a composition selected from the group consisting of cross-linked keratin crosslinked collagen and mixtures thereof, said membrane support being in contact at its opposite face with a reagent containing at least one precipitant present in a concentration effective in precipitating in the presence of a dermal irritant and at least one stabilizer present in a concentration effective to prevent precipitation of the precipitant in the absence of a dermal irritant, said reagent comprising an aqueous medium of pH and ionic strength compatible with said membrane support;

(c) measuring the amount of precipitate formed in the reagent; and (d) comparing the amount of precipitate formed with the amount of precipitate released using comparable amounts of a known dermal irritant in said mixture.

10. A method for determining the phototoxicity of a material to human skin or membrane which method comprises:

(a) exposing said material to ultraviolet light;

(b) applying said material to one face of a membrane support which mimics human skin or membrane to be tested comprising a base membrane support to which is bound a composition selected from the group consisting of cross-linked keratin, cross-linked collagen and mixtures thereof to which a dye is covalently bound wherein said dye is released from said covalent bonding in the presence of a dermal irritant, said membrane support being in contact at its opposite face with a reagent which comprises an aqueous medium of pH and ionic strength compatible with said membrane support;

(c) measuring the amount of dye formed in the reagent; and (d) comparing the amount of dye released with the amount of dye released in the absence of exposing said material to ultraviolet light.

11. A method for determining the phototoxicity of a material to human skin or membrane which method comprises:

(a) applying said material to one face of a membrane support which mimics human skin or membrane to be tested comprising a base membrane support to which is bound a composition selected from the group consisting of cross-linked keratin, cross-linked collagen and mixtures thereof to which a dye is covalently bound wherein said dye is released from said covalent bonding the presence of a dermal irritant, said membrane support being in contact at its opposite face with a reagent which comprises an aqueous medium of pH and ionic strength compatible with said membrane support;

(b) exposing said treated membrane support to ultraviolet light;

(c) measuring the amount of dye released into the reagent; and (d) comparing the amount of dye released with the amount of dye released in the absence of exposing said material to ultraviolet light.

12. A method to determine the effect of a test material on the ability of an irritant to exhibit dermal toxicity which method comprises:

(a) combining said test material with said irritant to obtain a mixture;

(b) applying said material to one face of a membrane support which mimics human skin or membrane to be tested comprising a base membrane support to which is bound a composition selected from the group consisting of cross-linked keratin, cross-linked collagen and mixtures thereof to which a dye is covalently bound wherein said dye is released from said covalent bonding the presence of a dermal irritant, said membrane support being in contact at its opposite face with a reagent which comprises an aqueous medium of pH and ionic strength compatible with said membrane support;

(c) measuring the amount of dye released into the reagent; and (d) comparing the amount of dye released with the amount of dye released using comparable amounts of a known dermal irritant in said mixture.

13. The method of any one of claims 1–12 wherein said membrane support is cellulose or nitrocellulose.

14. The method of any one of claims 1–9 wherein the reagent further includes a composition which interacts with a precipitant to increase its aggregation in the presence of dermal irritants.

15. The method of any one of claims 1–12 wherein said reagent has a pH between 2 and 9.

16. The method of any one of claims 1–12 wherein said reagent has an ionic strength of about 0.05 M to about 0.5 M.

17. The method of any one of claims 1–4 wherein the amount of dye released and precipitate formed is measured separately.

18. The method of any one of claims 1–12 wherein said known dermal irritant is sodium lauryl sulfate.

19. The method of any one of claims 1–4, 6 or 7–9 wherein said precipitate contains at least one globulin.

20. The method of any one of claims 1–12 wherein said membrane also has attached lipid moieties bound, covalently attached, or naturally present.

21. The method of any one claims 1, 2, 4–6, 10 11 or 12 wherein said dye is a carboxylic dye.

22. A method for determining the toxicity of a material to human mucous membranes which method comprises:

(a) applying said material to one face of a membrane in contact with, at its opposite face, a reagent wherein said membrane mimics human mucous membrane to be tested and through which said material can diffuse or permeate or through which said components of the reagent can diffuse to interact with the test material;

said reagent comprising at least one precipitant present in a concentration effective in precipitating in the presence of a mucosal irritant and said reagent further containing at least one stabilizer in a concentration effective in preventing precipitation of the precipitant in the absence of a mucosal irritant; and (b) measuring the amount of precipitate produced and comparing this to be amount of precipitate formed with a known mucosal irritant.

23. A membrane/reagent system comprising, a membrane support which comprises a base support said base support comprising cellulose or nitrocellulose to which is bound cross-linked keratin, cross-linked collagen, or mixtures thereof wherein said membrane support mimics skin or other animal membrane to be tested formed into a well secured by a ring into which a sample to be tested for dermal irritancy or anti-irritancy is applied, and a reagent contained in a receptacle into which said membrane support is well received.

24. The membrane/reagent system of claim 23 wherein a carboxylic dye is covalently linked to said membrane support.

25. The membrane/reagent system of claim 23 wherein a carboxylic dye is covalently linked to said membrane support.

26. The membrane/reagent system of claim 23 wherein a fluorescent dye is covalently linked to said membrane support.

27. The membrane/reagent system of claim 23 wherein said reagent comprises at least one precipitant present in a concentration effective to cause precipitation when a dermal irritant is applied to said membrane support and at least one stabilizer present in a concentration effective to prevent precipitation of the precipitant in the absence of dermal irritant and an aqueous medium to provide a clear aqueous liquid of pH and ionic strength compatible with said membrane support.

28. The membrane/reagent system of claim 27 wherein said precipitant is globular protein.

29. The membrane/reagent system of claim 28 wherein said globular protein is G1, G2, or G3.

30. The membrane/reagent system of claim 27 wherein said reagent further comprises a composition which interacts with the precipitant to increase its aggregation in the presence of dermal irritants.

31. The membrane/reagent system of claim 23 wherein lipid moieties are covalently bound or attached to said membrane support.

32. A device for in vitro determination of the dermal toxicity of a test material, said device having two chambers, each in contact with and separated from one another by a membrane support, the first chamber adapted to receive a sample of the test material, and the membrane containing cross-linked collagen or cross-linked keratin and being permeable to products of degradation of said collagen or keratin generated by contact of the membrane with the sample, and said second chamber containing a reagent capable of giving an indication of the passage of said degradation products through said membrane into said second chamber.

33. A method for determining the toxicity of a material to human skin or membrane which method comprises:
  (a) applying said material to one face of a base membrane support to which a dye is covalently bound wherein said dye is released from said covalent bonding in the presence of a dermal irritant, said membrane support being in contact at its opposite face with a reagent which comprises an aqueous medium of pH and ionic strength compatible with said membrane support;
  (b) measuring at least one of the amount of dye released into the reagent and the amount of precipitate formed in the reagent; and
  (c) comparing at least one of the amount of dye and precipitate with the amount of dye and precipitate released using comparable amounts of a known dermal irritant.

34. A method to determine the effect of a test material on the ability of an irritant to exhibit mucosal toxicity which method comprises:
  (a) combining said test material with said irritant to obtain a mixture;
  (b) applying said mixture to one face of a membrane in contact with a reagent at its opposite face,
  wherein said membrane support mimics human mucous membrane to be tested and through which said material can diffuse or permeate or through which said components of the reagent can diffuse to interact with the test material;
  said reagent comprising at least one precipitant present in a concentration effective in precipitating in the presence of a mucosal irritant and said reagent further containing at least one stabilizer in a concentration effective in preventing precipitation of the precipitant in the absence of a mucosal irritant; and
  (c) measuring the amount of precipitate produced and comparing this to the amount of precipitate formed with a known mucosal irritant in said mixture.

* * * * *